United States Patent
Oohara

(10) Patent No.: US 8,611,625 B2
(45) Date of Patent: Dec. 17, 2013

(54) TOMOGRAPHIC APPARATUS

(75) Inventor: Hiroshi Oohara, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 650 days.

(21) Appl. No.: 12/741,256

(22) PCT Filed: Nov. 29, 2007

(86) PCT No.: PCT/JP2007/073090
§ 371 (c)(1),
(2), (4) Date: Jul. 14, 2010

(87) PCT Pub. No.: WO2009/069215
PCT Pub. Date: Jun. 4, 2009

(65) Prior Publication Data
US 2010/0272319 A1   Oct. 28, 2010

(51) Int. Cl.
*G06K 9/00* (2006.01)
(52) U.S. Cl.
USPC .............................................. 382/131; 705/2
(58) Field of Classification Search
USPC ........................................................ 382/131
See application file for complete search history.

(56) References Cited

U.S. PATENT DOCUMENTS

| 4,833,698 | A | * | 5/1989 | Flannery et al. | ................. 378/19 |
| 2002/0082504 | A1 | * | 6/2002 | Mizushima et al. | .......... 600/477 |
| 2005/0013414 | A1 | | 1/2005 | Sun et al. | |

* cited by examiner

*Primary Examiner* — Hiep V Nguyen
(74) *Attorney, Agent, or Firm* — Cheng Law Group, PLLC

(57) ABSTRACT

The tomographic apparatus of this invention has an attenuation quantity calculating and adjusting unit, a filter length calculating unit, an attenuation correction function calculating unit and a transmission length calculating unit in an arithmetic processing unit. Thus, sectional images with a beam hardening correction can be acquired. The beam hardening correction can be made without using an iterative method. The attenuation correction function calculating unit calculates a correction function by approximating and expressing the correction function by a linear function linking, between two transmission lengths, ratios between measured attenuation quantities for two transmission lengths measured by an X-ray detector, and calculated attenuation physical quantities calculated and adjusted for these transmission lengths.

4 Claims, 5 Drawing Sheets

TOMOGRAPHIC APPARATUS

TECHNICAL FIELD

This invention relates to a tomographic apparatus for use in a CT apparatus, C-arm apparatus or the like.

BACKGROUND ART

X-rays used in a CT apparatus and the like do not have single energy, but are polychromatic X-rays which are a mixture of X-rays with various energies. Generally, X-rays with low energy attenuate easily through an interaction with a transmission substance, compared with X-rays with high energy. Therefore, with progress of transmission through a substance, an energy distribution of X-rays tends to show a high energy side remaining, which does not easily attenuate. As a result, an attenuation coefficient for polychromatic X-rays is not constant, but gradually becomes small. Such phenomenon is called "beam hardening phenomenon".

FIG. 7 is a graph schematically showing a correlation between the length of a transmission substance (hereinafter abbreviated as "transmission length") and the X-ray detection signal ratio between pre-transmission and post-transmission (hereinafter defined as "quantity of attenuation"). In FIG. 7, the horizontal axis represents transmission length K while the vertical axis with a logarithmic scale represents the quantity of attenuation. Monochromatic X-rays describe a straight line as shown in a dotted line in FIG. 7 since detection signal values are expressed by an exponential function having the transmission length K as the variable. It is seen, however, that polychromatic X-rays describe a curve which extends in a direction of the less attenuation resulting from the longer transmission length K as shown in a solid line in FIG. 7.

Generally, in CT reconstruction, a transmission length is converted from attenuation (that is, the quantity of attenuation) of detection signal values, and a distribution of transmission substances is obtained by solving an inverse problem. If a transmission length is calculated based on a consideration that attenuation is fixed without taking the beam hardening phenomenon into consideration, the transmission length cannot be calculated accurately. And CT reconstruction images will have, appearing thereon, artifacts due to a cupping phenomenon, for example, in which CT values lower in the central parts of the reconstruction images. Therefore, the beam hardening phenomenon must be taken into consideration when converting attenuation of the detection signal values into a transmission length.

There is a technique of preparing beforehand a function that can convert attenuation of transmission signal values into a transmission length of a transmission substance, in which the X-ray transmission length of the transmission substance is changed variously, and attenuation of each detection signal value is measured to be used as a basis. Specifically, where $P_0$ is a detection signal value before attenuation (that is, a detection signal value before transmission) corresponding to zero transmission length of the transmission substance, and P is a detection signal value after transmission, the quantity of attenuation is $P/P_0$ based on the above definitions, and an attenuation value Ln is derived from a definition $Ln=-\ln(P/P_0)$. ln is a natural logarithmic function. Using attenuation values measured when the transmission length is changed variously, and an inverse function is obtained beforehand as approximate function.

There is also a technique of correcting beam hardening, which adjusts a detection signal energy distribution of a system by measuring data of two phantoms and adjusting transmission lengths of two filters (see Patent Document 1, for example).

[Patent Document 1]
Specification of United States Patent Application Publication No. 2005/0013414

DISCLOSURE OF THE INVENTION

Problem to be Solved by the Invention

However, with the technique of obtaining a transmission length using an approximate function, there are several unknown coefficients, actual measurement is needed for data at least corresponding to the number of coefficients as attenuation value measurement data. Thus, there is a problem that it takes time and effort in data collection, and the burden is large. With Patent Document 1 noted above, an iterative method is required to determine transmission lengths of the two filters.

This invention has been made having regard to the state of the art noted above, and its object is to provide a tomographic apparatus which can correct beam hardening without using an iterative method.

Means for Solving the Problem

To fulfill the above object, this invention provides the following construction.

A tomographic apparatus of this invention is a tomographic apparatus for acquiring a sectional image by tomography, comprising (a) an attenuation physical quantity measuring device for measuring an attenuation physical quantity which is a physical quantity relating to attenuation due to transmission of X-rays; (b) an attenuation physical quantity calculating and adjusting device for calculating and adjusting a calculated attenuation physical quantity which is the attenuation physical quantity as calculated, by assuming a filter length having a predetermined value; (c) a filter length calculating device for finally calculating and adjusting the calculated attenuation physical quantity by calculating and determining a filter length which provides an agreement between a measured attenuation physical quantity for a transmission length which is the attenuation physical quantity measured by the attenuation physical quantity measuring device, and a calculated attenuation physical quantity for the transmission length calculated and adjusted by the attenuation physical quantity calculating and adjusting device; (d) a correction function calculating device for calculating a correction function for correcting the attenuation physical quantity based on ratios between measured attenuation physical quantities for at least two transmission lengths measured by the attenuation physical quantity measuring device and calculated attenuation physical quantities for these transmission lengths finally calculated and adjusted; and (e) a transmission length calculating device for calculating a transmission length of a transmission substance needed for tomography, based on the attenuation physical quantity corrected by the correction function calculated by the correction function calculating device, and with an inverse function of a transmission length to attenuation physical quantity conversion function for conversion into the attenuation physical quantity; the sectional image being acquired based on the transmission length calculated by the transmission length calculating device.

According to the tomographic apparatus of this invention, (a) the attenuation physical quantity measuring device measures an attenuation physical quantity which is a physical quantity relating to attenuation due to transmission of X-rays. On the other hand, an attenuation physical quantity is calculable by a predetermined equation. There is a disagreement between the attenuation physical quantity calculated (calculated attenuation physical quantity) and the measured attenuation physical quantity which is obtained by actual measurement.

Then, (b) the attenuation physical quantity calculating and adjusting device calculates and adjusts a calculated attenuation physical quantity which is the attenuation physical quantity as calculated, by assuming a material not considered, and assuming a filter length having a predetermined value for a filter of this material. (c) The filter length calculating device calculates and determines a filter length which provides an agreement between a measured attenuation physical quantity for a transmission length which is the attenuation physical quantity measured by the attenuation physical quantity measuring device, and a calculated attenuation physical quantity for the transmission length calculated and adjusted by the attenuation physical quantity calculating and adjusting device. The calculated attenuation physical quantity is finally calculated and adjusted by the filter length determined by the filter length calculating device in this way. By finally calculating and adjusting the calculated attenuation physical quantity in this way, with the transmission length used by the above filter length calculating device, no difference occurs between the attenuation physical quantities having the measured value and calculated value. However, with other transmission lengths, a difference can occur between the attenuation physical quantites having measured values and calculated values.

Then, (d) the correction function calculating device calculates a correction function for correcting the attenuation physical quantity based on ratios between measured attenuation physical quantities for at least two transmission lengths measured by the attenuation physical quantity measuring device and calculated attenuation physical quantities for these transmission lengths finally calculated and adjusted. By correcting the attenuation physical quantity with the correction function calculated by the correction function calculating device, the attenuation physical quantity can be calculated accurately with no difference occurring, with other transmission lengths, between the attenuation physical quantities having the measured value and calculated value. Based on this attenuation physical quantity, (e) the transmission length calculating device calculates a transmission length of a transmission substance needed for tomography, with an inverse function of a transmission length to attenuation physical quantity conversion function for conversion into the attenuation physical quantity, whereby the transmission length can be calculated accurately.

A beam hardening correction can be effected by acquiring a sectional image based on this transmission length, thereby to maintain uniformity of the sectional image without being influenced by cupping. The beam hardening correction can be carried out without using an iterative method as used in Patent Document 1 described hereinbefore.

In one example of the tomographic apparatus of this invention, the correction function calculating device calculates the correction function by approximating and expressing the above correction function by a linear function linking, between two transmission lengths, the ratios between measured attenuation physical quantities for two transmission lengths measured by the attenuation physical quantity measuring device, and calculated attenuation physical quantities for these transmission lengths calculated and adjusted by the attenuation physical quantity calculating and adjusting device. With this example, the correction function can be calculated simply, only by substituting it into a linear expression. Of course, the correction function calculating device may calculate the correction function by obtaining the correction function by a least square method using ratios between the measured attenuation physical quantities for at least two transmission lengths measured by the attenuation physical quantity measuring device, and the calculated attenuation physical quantities for these transmission lengths calculated and adjusted by the attenuation physical quantity calculating and adjusting device. In this case, the correction function can be obtained with increased accuracy.

In another example of the tomographic apparatus of this invention, both the filter length calculating device and the correction function calculating unit use a measured attenuation physical quantity for one transmission length of measured attenuation physical quantities for at least two transmission lengths measured by the attenuation physical quantity measuring device. With this example, the measurement by the attenuation physical quantity measuring device can be reduced by one time for the shared use of the measured attenuation physical quantity for one transmission length. Of course, such shared use is not necessary. However, a sectional image finally acquired has a major influence of the measured attenuation physical quantities for the transmission lengths used by the correction function calculating device, but has almost no influence of the measured attenuation physical quantity for the transmission length used by the filter length calculating device. Thus, the shared use is preferable.

Effects of the Invention

With the tomographic apparatus according to this invention, sectional images with a beam hardening correction can be acquired by providing the devices (a)-(e). The beam hardening correction can be made without using an iterative method.

DESCRIPTION OF REFERENCES

2 . . . X-ray detector
32 . . . filter length calculating unit
33 . . . attenuation quantity calculating and adjusting unit
34 . . . attenuation correction function calculating unit
35 . . . transmission length calculating unit

EMBODIMENT

Figure 1:
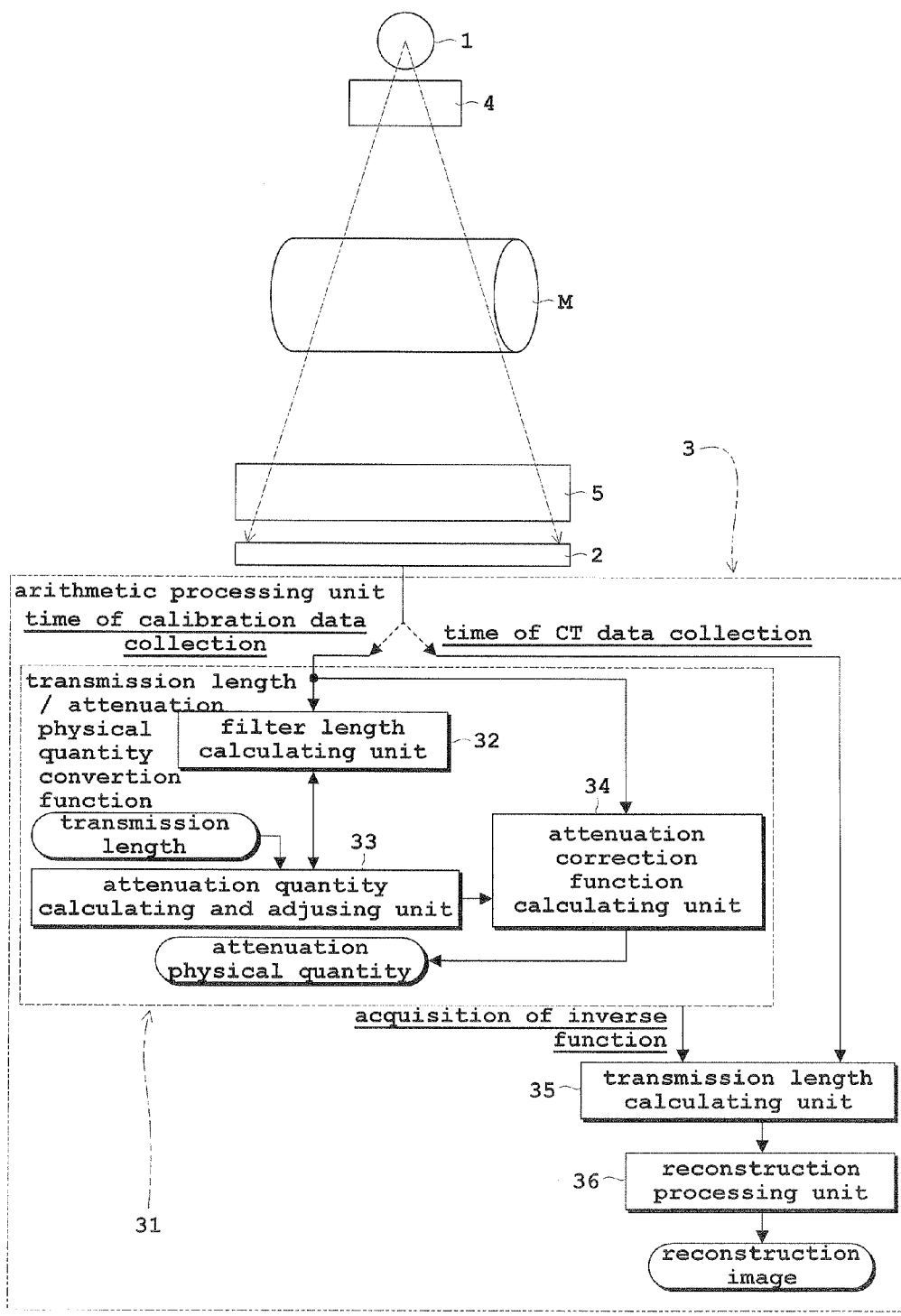
FIG. 1 is a schematic view and block diagram of an X-ray CT apparatus.
Figure 2:
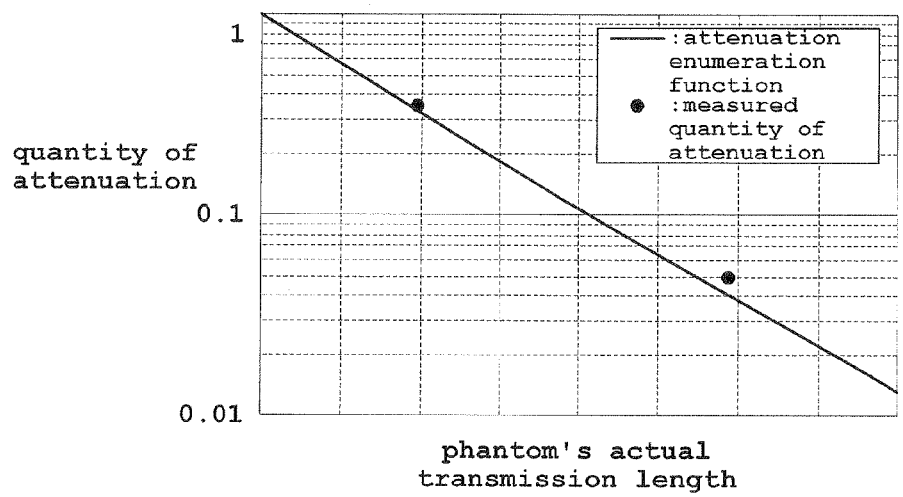
FIG. 2 is a graph schematically showing a correlation between calculated quantity of attenuation and transmission length, and also showing measured quantities of attenuation.
Figure 3:
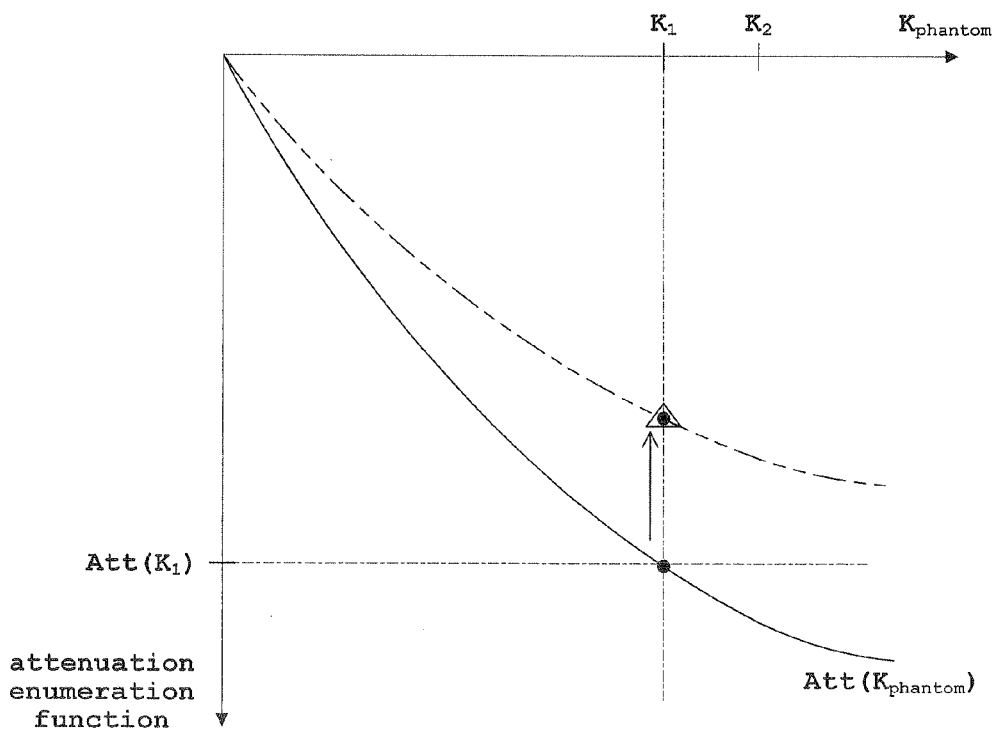
FIG. 3 is a graph for illustrating a case of calculating and determining a filter length after supposing a filter length, and calculating and adjusting a calculated quantity of attenuation.
Figure 4:
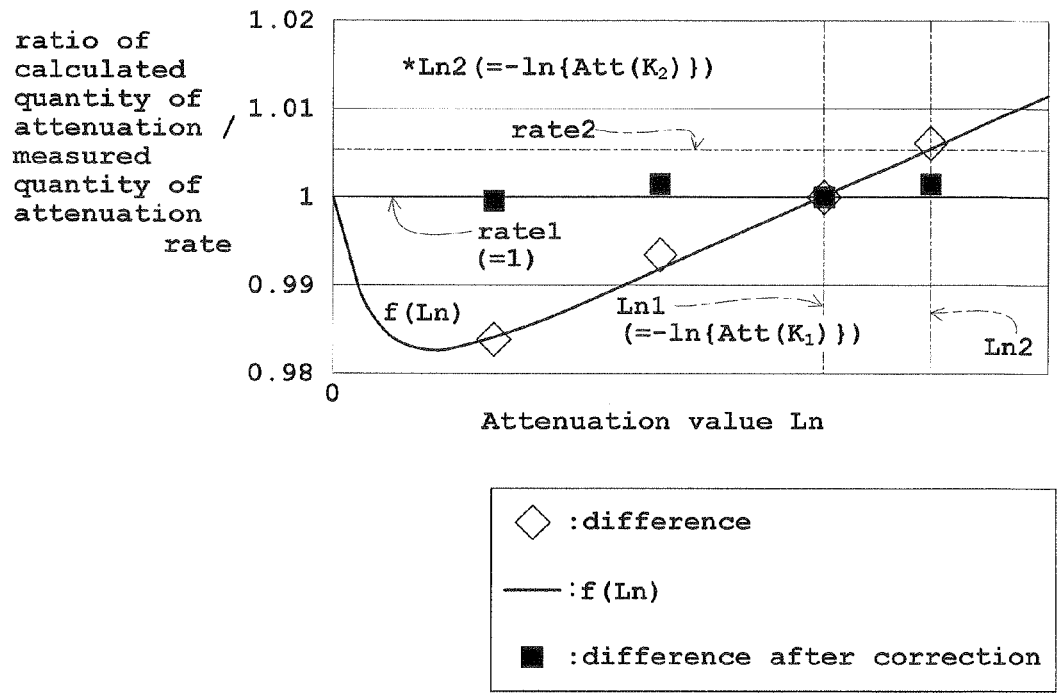
FIG. 4 is a graph schematically showing a correlation between attenuation value and ratio of calculated quantity of attenuation/measured quantity of attenuation.

An embodiment of this invention will be described hereinafter with reference to the drawings. FIG. 1 is a schematic view and block diagram of an X-ray CT apparatus. FIG. 2 is a schematically graph showing a correlation between calculated quantity of attenuation and transmission length, and also showing measured quantities of attenuation. FIG. 3 is a graph for illustrating a case of calculating and determining a filter length after supposing a filter length, and calculating and adjusting a calculated quantity of attenuation. FIG. 4 is a graph schematically showing a correlation between attenuation value and ratio of calculated quantity of attenuation/measured quantity of attenuation.

The X-ray CT apparatus according to this embodiment includes an X-ray tube 1 for emitting X-rays, an X-ray detector 2 for detecting the X-rays emitted from the X-ray tube 1 and transmitted through a subject M and the like, and an arithmetic processing unit 3 for performing various arithmetic processes based on detection signals of the X-rays detected by the X-ray detector 2. The X-ray tube 1 and X-ray detector 2 are constructed revolvable around the subject M by a gantry not shown. The subject M for normal CT data collection is a human body, but a phantom such as an acrylic plate is used at a time of calibration data collection.

The X-ray detector 2 detects the X-rays by converting into charge signals the X-rays emitted from the X-ray tube 1, transmitted through a collimator 4, subject M and a detector cushioning material 5, and incident on a detecting plane, further converting the charge signals into electric signals (detection signals), and measuring their values. Based on detection signal values emitted from the X-ray tube 1 and directly under the X-ray tube 1 (detection signal values before transmission) and detection signal values measured by the X-ray detector 2 (detection signal values after transmission), it is possible to measure a quantity of attenuation which is a detection signal ratio between the X-rays before transmission and after transmission. The X-ray detector 2 corresponds to the attenuation physical quantity measuring device in this invention.

The arithmetic processing unit 3 is composed of a central processing unit (CPU) and others. The arithmetic processing unit 3 has a transmission length to attenuation physical quantity conversion function 31 for converting into an attenuation physical quantity (a quantity of attenuation in this embodiment) a transmission length of a transmission substance needed for tomography (CT data collection) at a time of calibration data collection, and this transmission length to attenuation physical quantity conversion function 31 has a filter length calculating unit 32, an attenuation quantity calculating and adjusting unit 33 and an attenuation correction function calculating unit 34. In addition, the arithmetic processing unit 3 has a transmission length calculating unit 35 and a reconstruction processing unit 36 for the time of CT data collection.

The attenuation quantity calculating and adjusting unit 33, by assuming a filter length having a predetermined value (which is filter length $K_{imaginary}$ in this embodiment to be described hereinafter), calculates and adjusts a calculated attenuation physical quantity (calculated quantity of attenuation in this embodiment) which is an attenuation physical quantity (quantity of attenuation in this embodiment) calculated. The filter length calculating unit 32 finally calculates and adjusts the calculated attenuation physical quantity (calculated quantity of attenuation in this embodiment) by calculating and determining the filter length $K_{imaginary}$ which provides an agreement between a measured attenuation physical quantity (measured quantity of attenuation in this embodiment) for a transmission length which is an attenuation physical quantity (quantity of attenuation in this embodiment) measured by the X-ray detector 2 noted above, and the calculated quantity of attenuation through this transmission length calculated and adjusted by the attenuation quantity calculating and adjusting unit 33 noted above. The attenuation correction function calculating unit 34 calculates a correction function for correcting the quantity of attenuation (which is attenuation correction function f(Ln) in this embodiment to be described hereinafter) based on ratios between measured quantities of attenuation through at least two transmission lengths measured by the X-ray detector 2 and calculated quantities of attenuation through these transmission lengths finally calculated and adjusted (ratios of calculated quantities of attenuation/measured quantities of attenuation).

The transmission length calculating unit 35, based on the quantity of attenuation corrected by attenuation correction function f(Ln) calculated by the attenuation correction function calculating unit 34 noted above, calculates a transmission length of a transmission substance needed for tomography (CT data collection) by the X-ray CT apparatus, with an inverse function of the transmission length to attenuation physical quantity conversion function 31 (attenuation enumeration function Att ($K_{phantom}$) in this embodiment to be described hereinafter). The reconstruction processing unit 36 acquires a sectional image (reconstruction image in FIG. 1) through a reconstruction process based on the transmission length calculated by the transmission length calculating unit 35.

The filter length calculating unit 32 corresponds to the filter length calculating device in this invention. The attenuation quantity calculating and adjusting unit 33 corresponds to the attenuation physical quantity calculating and adjusting device in this invention. The attenuation correction function calculating unit 34 corresponds to the correction function calculating device in this invention. The transmission length calculating unit 35 corresponds to the transmission length calculating device in this invention. A specific function of each component in the arithmetic processing unit 3 will be described hereinafter.

The X-rays generated from the X-ray tube 1 are polychromatic X-rays as noted above, and their detection signal energy distribution is expressed by X(e) as the function of energy e. Attenuation of the X-rays after the X-rays are generated from the X-ray tube 1 and before they reach the subject M (e.g. such as through a filter inside the collimator 4) is expressed by the following equation (1) using a plurality of materials through which the X-rays are transmitted (linear attenuation coefficients $\mu_{prei}$ (e), where i=1, 2, 3, . . . ) and transmission lengths $K_{prei}$ thereof (where i=1, 2, 3, . . . ). Linear attenuation coefficients $\mu_{prei}$ (e) have known values corresponding to the materials, and transmission lengths $K_{prei}$ also are known from the length of the filter inside the collimator 4.

[Math 1]

$$\exp[-\{\mu_{pre1}(e) \cdot K_{pre1} + \mu_{pre2}(e) \cdot K_{pre2} + \mu_{pre3}(e) \cdot K_{pre3} + \ldots \}] \quad (1)$$
$$\left( = \exp\left[-\sum_{i=1} \{\mu_{prei}(e) \cdot K_{prei}\}\right]\right)$$

Similarly, attenuation of the X-rays after being transmitted through the subject M and before they reach the X-ray detector 2 (e.g. through the detector cushioning material 5) is expressed by the following equation (2) using a plurality of materials through which the X-rays are transmitted (linear attenuation coefficients $\mu_{posti}$ (e), where i=1, 2, 3, . . . ) and transmission lengths $K_{posti}$ thereof (where i=1, 2, 3, . . . ). Linear attenuation coefficients $\mu_{pesti}$ (e) have known values corresponding to the materials, and transmission lengths $K_{posti}$ also are known from the length of the detector cushioning material 5.

[Math 2]

$$\exp[-\{\mu_{post1}(e) \cdot K_{post1} + \mu_{post2}(e) \cdot K_{post2} + \mu_{post3}(e) \cdot K_{post3} + \ldots \}] \quad (2)$$

$$\left( = \exp\left[-\sum_{i=1}\{\mu_{posti}(e) \cdot K_{posti}\}\right] \right)$$

And the conversion from the X-rays to the detection signals in the X-ray detector 2 is expressed by $e \cdot [1-\exp\{-\mu_{det}(e) \cdot K_{det}\}]$ using the material of the detector (linear energy absorption coefficient $\mu_{det}$ (e)) and its thickness $K_{det}$. This linear energy absorption coefficient met (e) also has a known value corresponding to the material, and thickness $K_{det}$ also is known from the thickness of X-ray detector 2.

From the above, when there is no subject M, a detection signal energy distribution Signal (e) is expressed by the following equation (3) using equation (1) and equation (2) above.

[Math 3]

$$\begin{aligned}
\text{signal}(e) = & X(e) \cdot \\
& \exp[-\{\mu_{pre1}(e) \cdot K_{pre1} + \mu_{pre2}(e) \cdot K_{pre2} + \mu_{pre3}(e) \cdot K_{pre3} + \ldots\}] \cdot \\
& \exp[-\{\mu_{post1}(e) \cdot K_{post1} + \mu_{post2}(e) \cdot K_{post2} + \mu_{post3}(e) \cdot K_{post3} + \ldots\}] \cdot \\
& e \cdot [1 - \exp\{-\mu_{det}(e) \cdot K_{det}\}] \\
= & X(e) \cdot \\
& \exp\left[-\sum_{i=1}\{\mu_{prei}(e) \cdot K_{prei}\}\right] \cdot \\
& \exp\left[-\sum_{i=1}\{\mu_{posti}(e) \cdot K_{posti}\}\right] \cdot \\
& e \cdot [1 - \exp\{-\mu_{det}(e) \cdot K_{det}\}]
\end{aligned} \quad (3)$$

In equation (3) above, the conversion from the X-rays to the detection signals in the X-ray detector 2 may be calculated from $e \cdot [1-\exp\{-\mu'_{det}(e) \cdot K_{det}\}] \cdot \mu_{det}(e)/\mu'_{det}(e)$ using linear attenuation coefficient $\mu'_{det}$ (e) of the material of the detector, instead of $e \cdot [1-\exp\{-\mu_{det}(e) \cdot K_{det}\}]$. This linear attenuation coefficient $\mu'_{det}$ (e) also has a known value corresponding to the material.

If the detection signal energy distribution Signal (e) could be calculated accurately, attenuation of the X-rays in the material of the subject M (linear attenuation coefficient $\mu_{phantom}(e)$) and its transmission length $K_{phantom}$ would be expressed by $\exp[-\{\mu_{phantom}(e) \cdot K_{phantom}\}]$. Linear attenuation coefficient $\mu_{phantom}$ (e) has a known value corresponding to the material. The quantity of attenuation $P/P_0$ of the detection signals at that time can be calculated accurately with the Att ($K_{phantom}$) function (hereinafter called "attenuation enumeration function") in the following equation (4).

[Math 4]

$$Att(K_{phantom}) = \frac{\int Signal(e) \cdot \exp[-\{\mu_{phantom}(e) \cdot K_{phantom}\}] de}{\int Signal(e) de} \quad (4)$$

However, when the quantity of attenuation $P/P_0$ is measured by the X-ray detector 2, since the materials through which the X-ray are transmitted include also a material not taken into consideration, as shown in FIG. 2, there is a disagreement between the measured quantity of attenuation (see black dots in FIG. 2) and the calculated quantity of attenuation $P/P_0$ (=attenuation enumeration function Att ($K_{phantom}$)) (solid line in FIG. 2) derived from the above equation (4).

Then, the detection signal energy distribution Signal (e) is changed by newly assuming one type of material (linear attenuation coefficient $\mu_{imaginary}$ (e)) not taken into consideration and assuming that transmission has taken place through its length $K_{imaginary}$. Specifically, an appropriate assumption is made of any one type of material selected from materials such as aluminum (Al), copper (Cu) and so on, for example, and linear attenuation coefficient $\mu_{imaginary}$ (e) of the assumed material is assumed. Or an assumption may be made by defining linear attenuation coefficient $\mu_{imaginary}$ (e) of an imaginary material which does not actually exist. Linear attenuation coefficient $\mu_{imaginary}$ (e) has a known value corresponding to the assumed material. In the following equation (5), Signal (e) of the right-hand side indicates the energy distribution derived from equation (3) above, and Signal (e) of the left-hand side indicates the energy distribution changed newly. That is, detection signal energy distribution Signal (e) is changed by substituting Signal (e) derived from equation (3) above into the right-hand side of the following equation (5), substituting the assumed linear attenuation coefficient $\mu_{imaginary}$ (e) and filter length $K_{imaginary}$ into the right-hand side of the following equation (5), and obtaining a value of Signal (e) of the left-hand side.

[Math 5]

$$\text{signal}(e) = \text{signal}(e) \cdot \exp[-\{\mu_{imaginary}(e) \cdot K_{imaginary}\}] \quad (5)$$

The attenuation quantity calculating and adjusting unit 33 of the arithmetic processing unit 3 assumes a filter length $K_{imaginary}$ having an arbitrary value according to equation (5) above, and changes detection signal energy distribution Signal (e) to the left-hand side in equation (5) above. And the attenuation quantity calculating and adjusting unit 33 calculates and adjusts the calculated quantity of attenuation by calculating attenuation enumeration function Att ($K_{phantom}$) for transmission length $K_{phantom}$ of the subject M from equation (4) above using the changed detection signal energy distribution Signal (e). Specifically, as shown in FIG. 3, filter length $K_{imaginary}$ is changed to bring into agreement the quantity of attenuation through a certain transmission length $K_1$ measured by the X-ray detector 2 (measured quantity of attenuation) (see the white triangle in FIG. 3), and calculated quantity of attenuation Att ($K_1$) through the transmission length $K_1$ (see the black dot on the solid line in FIG. 3). With the setting change to the filter length $K_{imaginary}$, detection signal energy distribution Signal (e) also is changed by equation (5) above, With this, the calculated quantity of attenuation Att ($K_1$) also is adjusted by equation (5) and equation (4) above, and the calculated quantity of attenuation Att ($K_1$) adjusted approaches in a direction indicated by an arrow in FIG. 3 to agree with the measured quantity of attenuation (see the black dot on the two-dot chain line in FIG. 3). The filter length calculating unit 32 of the arithmetic processing unit 3 calculates and determines this filter length $K_{imaginary}$ when an agreement is attained.

Thus, by calculating filter length $K_{imaginary}$ which provides an agreement between the measured quantity of attenuation through the above transmission length and the calculated quantity of attenuation through this transmission length, the attenuation quantity calculating and adjusting unit 33 finally calculates and adjusts attenuation enumeration function Att ($K_{phantom}$) for transmission length $K_{phantom}$ from the graph of the solid line in FIG. 3 to the graph of the two-dot chain line in FIG. 3. Since the measured quantity of attenuation and (calculated and adjusted) calculated quantity of attenuation Att ($K_1$) through the above transmission length $K_1$ are brought into agreement by this final calculation and adjustment, no difference occurs between quantities of attenuation in measured value and calculated value.

Once the attenuation quantity calculating and adjusting unit 33 finally calculates and adjusts attenuation enumeration function Att ($K_{phantom}$) for transmission length $K_{phantom}$ by calculating filter length $K_{imaginary}$ in this way, no difference will occur between the quantities of attenuation in measured value and calculated value for the above transmission length $K_1$. However, even if attenuation enumeration function Att ($K_{phantom}$) is finally calculated and adjusted, when a comparison is actually made with measurements, differences do occur, depending on conditions, between the quantities of attenuation in measured value and calculated value for other transmission lengths than transmission length $K_1$. As shown in FIG. 4, with a difference occurring with a change of an attenuation value being expressed by a ratio between calculated quantity of attenuation and measured quantity of attenuation, since calculated quantity of attenuation Att ($K_1$) for the above transmission length $K_1$ is finally calculated and adjusted to agree with the measured quantity of attenuation, the ratio between calculated quantity of attenuation and measured quantity of attenuation is "1" and there is no difference therebetween for natural logarithmic value [$-\ln \{$Att ($K_1$)$\}$] of calculated quantity of attenuation Att ($K_1$) through transmission length $K_1$ (that is, calculated attenuation value for transmission length $K_1$). However, it will be seen from the graph of FIG. 4 that a difference occurs in proportion to a distance of the attenuation value from the calculated attenuation value for transmission length $K_1$, which varies by a linear function as a whole.

Then, an attenuation correction function which shows this ratio between of calculated quantity of attenuation and measured quantity of attenuation is expressed here by function f(Ln) of calculated attenuation value Ln. Ratios between measured quantities of attenuation through at least two transmission lengths measured by the X-ray detector 2, and calculated quantities of attenuation through these transmission lengths finally calculated and adjusted, i.e. ratios between calculated quantity of attenuation and measured quantity of attenuation, are assumed to be (Ln1, rate1), (Ln2, rate2) and so on to correspond to calculated attenuation values Ln, respectively.

In this embodiment, the X-ray detector 2 measures quantities of attenuation through two transmission lengths $K_1$, $K_2$, and description will be made assuming that one of them, i.e. the measured quantity of attenuation through transmission length $K_1$, is used when the filter length calculating unit 32 noted hereinbefore calculates and determines filter length $K_{imaginary}$. That is, in this embodiment, the measured quantities of attenuation through the two transmission lengths $K_1$, $K_2$ are used when the attenuation correction function calculating unit 34, described hereinafter, of the arithmetic processing unit 3 calculates attenuation correction function f(Ln), and one of them, i.e. the measured quantity of attenuation through transmission length $K_1$ is used when the filter length calculating unit 32 calculates and determines filter length $K_{imaginary}$.

The attenuation correction function calculating unit 34 of the arithmetic processing unit 3 sets (Ln1, rate1), (Ln2, rate2) respectively corresponding to calculated attenuation values Ln, which are ratios between the measured quantities of attenuation through the two transmission lengths $K_1$, $K_2$ measured by the X-ray detector 2, and calculated quantities of attenuation Att ($K_1$), Att ($K_2$) through these transmission lengths $K_1$, $K_2$ finally calculated and adjusted (i.e. ratios between calculated quantity of attenuation and measured quantity of attenuation). That is, in this embodiment, since the ratio of calculated quantity of attenuation Att ($K_1$)/measured quantity of attenuation through transmission length $K_1$ is rate1, and calculated quantity of attenuation Att ($K_1$) through transmission length $K_1$ is calculated and adjusted to agree with the measured quantity of attenuation, the ratio rate 1 of calculated quantity of attenuation Att ($K_1$)/measured quantity of attenuation through transmission length $K_1$ is "1". The calculated attenuation value for transmission length $K_1$ is Ln1, and calculated attenuation value Ln1 for transmission length $K_1$ is expressed by "$-\ln \{$Att ($K_1$)$\}$". The ratio of calculated quantity of attenuation Att ($K_2$)/measured quantity of attenuation through transmission length $K_2$ is rate2, and calculated attenuation value Ln2 through transmission length $K_2$ is expressed by "$-\ln \{$Att ($K_2$)$\}$".

As described above, attenuation correction function f(Ln) differing from calculation attenuation value Ln1 ($=-\ln \{$Att ($K_1$)$\}$) for transmission length $K_1$ is expressed by a linear function. That is, attenuation correction function f(Ln) is expressed by a linear expression linking (Ln1, rate1), (Ln2, rate2) for transmission lengths $K_1$, $K_2$. And when the calculated attenuation value is "0", attenuation correction function f(Ln) can be expressed by the following equation (6) in order to return the ratio of calculated quantity of attenuation/measured quantity of attenuation to "1". τ is an appropriate time constant for returning the ratio of calculated quantity of attenuation/measured quantity of attenuation to "1" when the calculated attenuation value is "0". This time constant τ may be determined by measuring a quantity of attenuation corresponding to an attenuation value close to "0" and using the measured quantity of attenuation.

[Math 6]

$$f(\text{Ln}) = 1 + \left\{1 - \exp\left(-\frac{\text{Ln}}{\tau}\right)\right\} \cdot \left\{\frac{\text{rate2} - \text{rate1}}{\text{Ln2} - \text{Ln1}} \cdot (\text{Ln} - \text{Ln1}) + \text{rate1} - 1\right\} \quad (6)$$

The term of the exponential function in equation (6) above is set, when the calculated attenuation value is "0", to draw a curve, as shown in FIG. 4, from calculated attenuation value at "0" to calculated attenuation value Ln1 for transmission length $K_1$ in order to return the ratio of calculated quantity of attenuation/measured quantity of attenuation to "1". That is, a curve is drawn as shown in FIG. 4, with the term of the exponential function being effective since the attenuation value is small from the calculated attenuation value at "0" to calculated attenuation value Ln1 for transmission length $K_1$. As a result, when the calculated attenuation value is "0", attenuation correction function f(Ln)=1 by substituting Ln=0 into equation (6) above, and thus the ratio of calculated quantity of attenuation/measured quantity of attenuation can be returned to "1". On the other hand, the attenuation value becomes large when calculated attenuation value Ln1 for transmission length $K_1$ is exceeded, as a result of which the term of the exponential function can substantially be disregarded, and attenuation correction function f(Ln) is expressed by a linear function.

After the attenuation correction function calculating unit 34 calculates attenuation correction function f(Ln) from equation (6) above, the quantity of attenuation is corrected using this attenuation correction function f(Ln). That is, attenuation enumeration function Att ($K_{phantom}$) for transmission length $K_{phantom}$, i.e. the quantity of attenuation through each transmission length $K_{phantom}$, is corrected by dividing attenuation enumeration function Att ($K_{phantom}$) finally calculated and adjusted by the quantity of attenuation calculating and adjusting unit 33, by attenuation correction function f(Ln) (=f[−ln {Att ($K_{phantom}$)}]) derived from equation (6) above. Thus, the quantity of attenuation can be calculated accurately without generating differences for other transmission lengths. The solid line in FIG. 4 is attenuation correction function f(Ln). The white rhombuses on the solid line in FIG. 4 are differences. The black rectangles in FIG. 4 are differences after correction. As seen from FIG. 4, the differences after correction are present substantially on "1" as the ratio of calculated quantity of attenuation/measured quantity of attenuation despite variations in the attenuation value, which shows that the differences are eliminated.

This corrected quantity of attenuation has a value dependent on the material (linear attenuation coefficient $\mu_{phantom}$ (e)) and transmission length $K_{phantom}$ of a phantom (e.g. acrylic plate) used as subject M at a time of calibration data collection. Then, in order to determine a transmission length of water which is a transmission substance needed for tomography (i.e. at a time of CT data collection) by the X-ray CT apparatus, a corrected attenuation physical quantity for transmission length $K_{phantom}$ of water (corresponding to the transmission length to attenuation physical quantity conversion function 31 in FIG. 1) can be calculated by using the linear attenuation coefficient of water instead of $\mu_{phantom}$ of the phantom material in equation (4) above using the same value as filter length $K_{imaginary}$, and from the division made by equation (6) above. The linear attenuation coefficient has a known value corresponding to the transmission substance as noted hereinbefore.

Also other transmission lengths than water needed for tomography (CT data collection) can be converted to attenuation physical quantities by the transmission length to attenuation physical quantity convertion function 31. Then, conversely, the transmission length of water is calculated from the attenuation physical quantity by the inverse function of transmission length to attenuation physical quantity conversion function 31.

From attenuation physical quantities matched with respective transmission lengths, a look-up table having the attenuation physical quantities as input and the transmission lengths as output is prepared for obtaining the inverse function of transmission length to attenuation physical quantity conversion function 31. Transmission length $K_{phantom}$ can be calculated accurately since transmission length $K_{phantom}$ is determined using the quantity of attenuation calculated accurately.

The transmission length calculating unit 35 of the arithmetic processing unit 9 calculates transmission length $K_{phantom}$ of water, using the look-up table, from the physical attenuation quantity.

As is clear from the above description, the quantity of attenuation and attenuation value correspond to the attenuation physical quantity in this invention. The filter length $K_{imaginary}$ corresponds to the filter length in this invention. Attenuation correction function f(Ln) corresponds to the correction function in this invention. The result of the division of attenuation enumeration function Att ($K_{phantom}$) by attenuation correction function f(Ln) corresponds to the transmission length to attenuation physical quantity conversion function in this invention.

Figure 5:
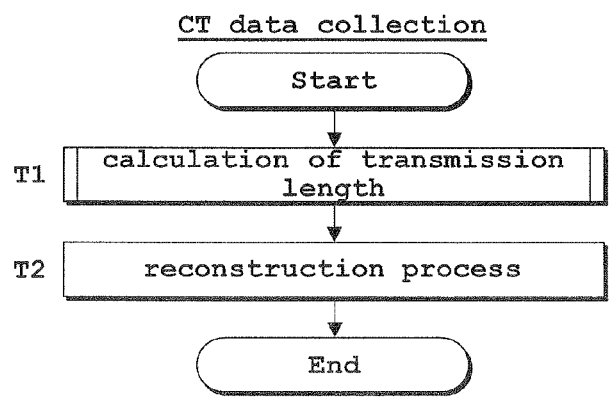
FIG. 5 is a flow chart showing a process of tomography (CT data collection) according to an embodiment.
Figure 6:
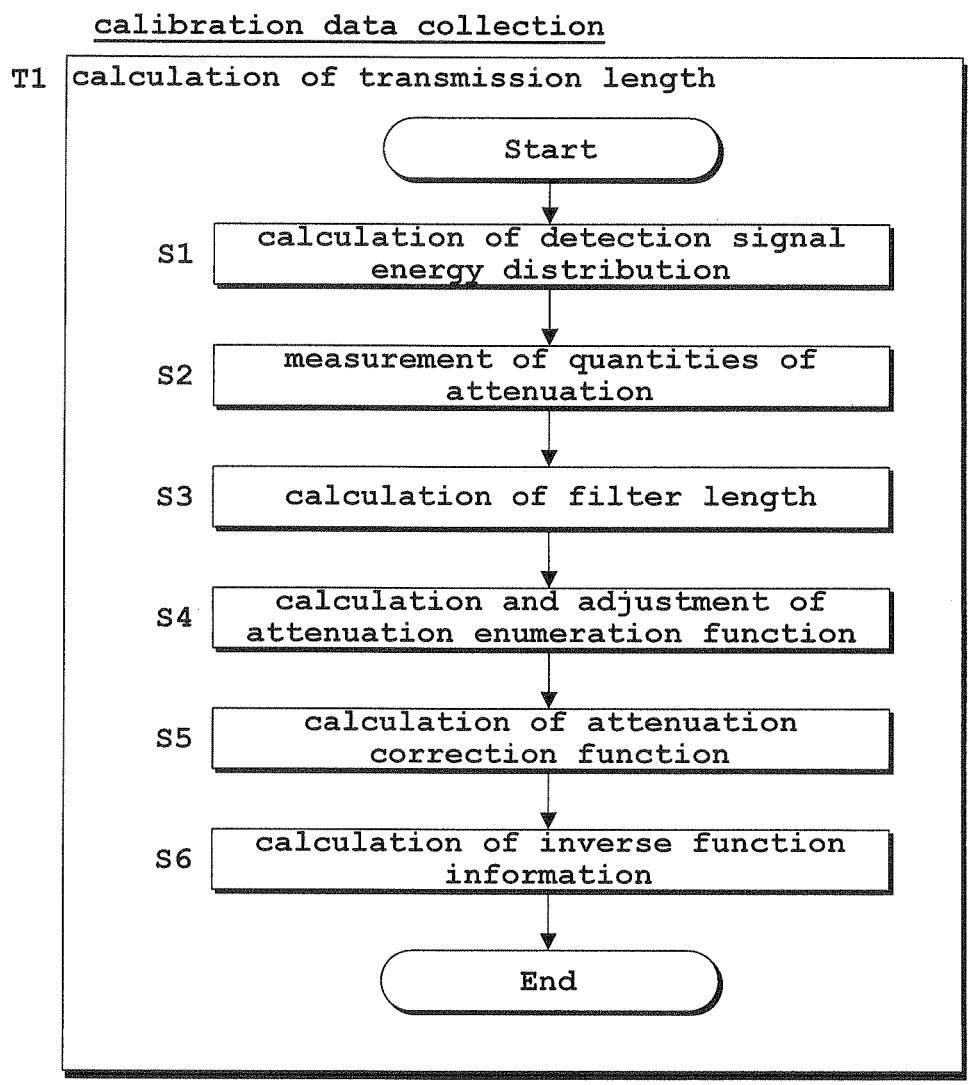
FIG. 6 is a flow chart showing a process of calibration data collection in a series of processes including tomography according to the embodiment.
Figure 7:
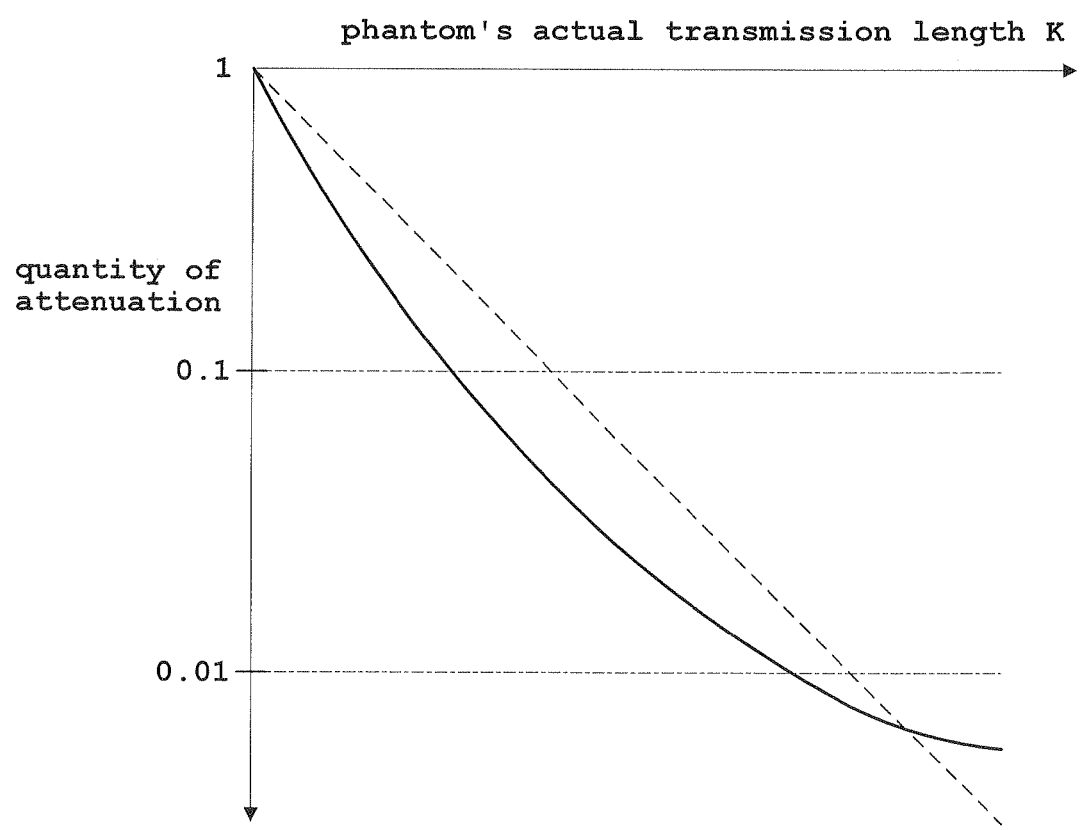
FIG. 7 is a graph schematically showing a correlation between calculated quantity of attenuation and transmission length.

Next, a series of processes including tomography according to this embodiment will be described with reference to FIGS. 5 and 6. FIG. 5 is a flow chart showing a process of tomography (CT data collection) according to the embodiment. FIG. 6 is a flow chart showing a process of calibration data collection in the series of processes including tomography according to the embodiment.

(Step T1) Calculation of Transmission Length

The transmission length calculating unit 35 calculates a transmission length of a transmission substance needed for tomography (CT data collection). For this purpose, calibration data is collected in the following steps S1-S6.

(Step S1) Calculation of Detection Signal Energy Distribution

A detection signal energy distribution Signal (e) is calculated using equation (3) above from sensitivity characteristics of the X-ray detector 2, X-ray spectrum and so on. This detection signal energy distribution Signal (e) is a parameter determined beforehand. Once the detection signal energy distribution Signal (e) is determined beforehand, it is not necessary to execute step S1 each time.

(Step S2) Measurement of Quantities of Attenuation

Phantom radiography is carried out for calibration data collection, using a phantom (acrylic plate or the like) as subject M. Specifically, quantities of attenuation are measured by the X-ray detector 2 by changing the transmission length each time. Regarding the quantities of attenuation measured as measured quantities of attenuation, the measured quantities of attenuation through at least two transmission lengths measured by the X-ray detector 2 are acquired. In this embodiment, the measured quantities of attenuation through two transmission lengths $K_1$, $K_2$ are acquired as noted hereinbefore.

(Step S3) Calculation of Filter Length

The attenuation quantity calculating and adjusting unit 33 changes the detection signal energy distribution Signal (e) in step S1 using equation (5) above, by assuming a material not taken into consideration and considering that a filter of that material is penetrated through appropriate filter length $K_{imaginary}$. The attenuation quantity calculating and adjusting unit 33 calculates and adjusts the calculated quantity of attenuation by calculating attenuation enumeration function Att ($K_{phantom}$) from equation (4) above using the changed detection signal energy distribution Signal (e). And the filter length calculating unit 32 calculates filter length $K_{imaginary}$ which provides an agreement between the measured quantity of attenuation through transmission length $K_1$ measured by the X-ray detector 2 in step S2 and the calculated quantity of attenuation Att ($K_1$) through that transmission length $K_1$.

(Step S4) Calculation and Adjustment of Attenuation Enumeration Function

Thus, the attenuation quantity calculating and adjusting unit 33 finally calculates and adjusts attenuation enumeration function Att ($K_{phantom}$) by calculating filter length $K_{imaginary}$ in step S3.

(Step S5) Calculation of Attenuation Correction Function

The attenuation correction function calculating unit 34 calculates attenuation correction function f(Ln) using equation (6) above based on the ratios between the measured quantities of attenuation through the two transmission lengths $K_1$, $K_2$ measured by the X-ray detector 2 in step S2, and calculated quantities of attenuation Att ($K_1$), Att ($K_2$) through these transmission lengths $K_1$, $K_2$ finally calculated and adjusted (step S4).

(Step S6) Calculation of Inverse Function Information

The linear attenuation coefficient of water which is the transmission substance needed for tomography is substituted into equation (4) above to calculate and adjust the quantity of attenuation through the transmission length of water, and a corrected quantity of attenuation is calculated by correcting the quantity of attenuation using attenuation correction function f(Ln) calculated in step S6. Corrected quantities of attenuation are calculated, through the same procedure, for other transmission lengths of that transmission substance. Prior to CT imaging (i.e. tomography by the X-ray CT apparatus), a look-up table for obtaining an inverse function (i.e. inverse function information) is prepared as having the corrected quantities of attenuation and each transmission length $K_{phantom}$ in a corresponding relationship. Once it is prepared, it is not necessary to repeat it before each CT imaging.

(Step T1) Calculation of Transmission Length

A transmission length is obtained from a quantity of attenuation or attenuation value using the look-up table prepared in step S6.

(Step T2) Reconstruction Process

And based on this transmission length, the reconstruction processing unit 36 acquires a sectional image (reconstruction image) by solving the inverse problem, carrying out a reconstruction process, and determining a distribution of transmission substances.

A beam hardening correction can be effected by acquiring a sectional image based on the transmission length accurately calculated in step T1, thereby to maintain uniformity of the sectional image without being influenced by cupping. The beam hardening correction can be carried out without using an iterative method as used in Patent Document 1 described hereinbefore. Compared with the conventional technique of determining a transmission length using an approximation function, only the number of determinations by the X-ray detector 2 matters, which produces also the effect of reducing the time and effort for collecting data and lightening the burden.

In this embodiment, as described above, the attenuation correction function calculating unit 34 calculates attenuation correction function f(Ln) by approximating and expressing attenuation correction function f(Ln) by a linear function linking, as (Ln1, rate1), (Ln2, rate2) between two transmission lengths $K_1$, $K_2$, the ratios between measured quantities of attenuation through the two transmission lengths $K_1$, $K_2$ measured by the X-ray detector 2, and calculated quantities of attenuation Att ($K_1$), Att ($K_2$) through these transmission lengths $K_1$, $K_2$. In this case, attenuation correction function f(Ln) can be calculated simply, only by substituting it into the linear expression.

In this embodiment, as described above, both the filter length calculating unit 32 and attenuation correction function calculating unit 34 use the measured quantity of attenuation through one transmission length $K_1$ of the measured quantities of attenuation through at least two transmission lengths $K_1$, $K_2$ measured by the X-ray detector 2. In this case, the measurement by the X-ray detector 2 can be reduced by one time for the shared use of the measured quantity of attenuation through one transmission length $K_1$.

This invention is not limited to the foregoing embodiment, but may be modified as follows:

(1) In the foregoing embodiment, the attenuation physical quantity processed by the attenuation physical quantity measuring device (X-ray detector 2 in the embodiment) and the attenuation physical quantity calculating and adjusting device (attenuation quantity calculating and adjusting unit 33 in the embodiment) is the quantity of attenuation expressed by the detection signal ratio between X-rays before transmission and after transmission. However, there is no limitation as to the attenuation physical quantity, as long as it is a parameter relating to attenuation as illustrated by the attenuation value which is a natural logarithmic value of the quantity of attenuation. There is no limitation as to also the attenuation physical quantity processed by the attenuation physical quantity measuring device and attenuation physical quantity calculating and adjusting device.

(2) In the foregoing embodiment, the correction function (attenuation correction function in the embodiment) is calculated using the measured attenuation physical quantities (measured quantities of attenuation in the embodiment) for two transmission lengths $K_1$, $K_2$ measured by the X-ray detector 2. However, as long as the measured attenuation physical quantities for at least two transmission lengths are used, the correction function may be calculated using measured attenuation physical quantities for three or more transmission lengths, for example. There is no limitation as to the number of measured attenuation physical quantities used as long as they are plural.

(3) In the foregoing embodiment, the correction function is calculated by approximating and expressing the correction function (attenuation correction function in the embodiment) with a linear function in the linear expression linking (Ln1, rate1), (Ln2, rate2) for two transmission length $K_1$, $K_2$ measured by the X-ray detector 2, but this is not limitative. The correction function may be calculated by obtaining the correction function by a least square method using (Ln1, rate1), (Ln2, rate2), (Ln2, rate3) for at least two transmission lengths (e.g. three transmission lengths $K_1$, $K_2$, $K_3$) measured by the X-ray detector 2. In this case, the correction function can be obtained with increased accuracy.

(4) In the foregoing embodiment, both the filter length calculating unit 32 and attenuation correction function calculating unit 34 use the measured quantity of attenuation through one transmission length $K_1$ of the measured quantities of attenuation through at least two transmission lengths $K_1$, $K_2$ ... measured by the X-ray detector 2, but such shared use is not absolutely necessary. However, where, for example, a measured quantity of attenuation through a transmission length is not shared, such that the filter length calculating unit

32 uses the measured quantity of attenuation through transmission length $K_1$ and the attenuation correction function calculating unit 34 uses the measured quantities of attenuation through two transmission lengths $K_2$, $K_3$, a sectional image finally acquired has a major influence of the measured quantities of attenuation through transmission lengths $K_2$, $K_3$ used by the attenuation correction function calculating unit 34, but has almost no influence of the measured quantity of attenuation through transmission length $K_1$ used by the filter length calculating unit 32. Thus, a shared use as in the embodiment is preferable.

(5) In the foregoing embodiment, the tomographic apparatus is an X-ray CT apparatus. However, this invention is applicable also to an apparatus which carries out tomography by means of a C-arm. Thus, there is no limitation as to the tomography apparatus to which this invention is applied.

The invention claimed is:

1. A tomographic apparatus for acquiring a sectional image, comprising:
   an attenuation quantity measuring device for measuring an X-ray attenuation quantity by emitting X-rays to a phantom having a known thickness;
   an attenuation quantity calculating device for calculating an X-ray attenuation quantity assuming X-rays are emitted to a filter formed of a predetermined material having the known thickness;
   a correction quantity calculating device for calculating as a correction quantity a ratio between the measured X-ray attenuation quantity and the calculated X-ray attenuation quantity;
   a correction function calculating device for calculating, based on correction quantities calculated with a plurality of known thicknesses, a correction function showing a relationship between the measured attenuation quantity and the correction quantity; and
   a transmission length calculating device for calculating a transmission length by acquiring from the correction function a correction quantity corresponding to an X-ray attenuation quantity measured by emitting X-rays to a subject, correcting the X-ray attenuation quantity measured by emitting X-rays to the subject with the acquired correction quantity, and converting the corrected X-ray attenuation quantity into a thickness of the predetermined material;
   the sectional image being acquired based on the transmission length.

2. The tomographic apparatus according to claim 1, wherein the correction function calculating device calculates the correction function by approximating and expressing the correction function by a linear function linking, between two transmission lengths, the ratios between measured attenuation physical quantities for two transmission lengths measured by the attenuation physical quantity measuring device, and calculated attenuation physical quantities for these transmission lengths calculated and adjusted by the attenuation physical quantity calculating and adjusting device.

3. The tomographic apparatus according to claim 1, wherein the correction function calculating device calculates the correction function by obtaining the correction function by a least square method using the ratios between measured attenuation physical quantities for at least two transmission lengths measured by the attenuation physical quantity measuring device, and calculated attenuation physical quantities for these transmission lengths calculated and adjusted by the attenuation physical quantity calculating and adjusting device.

4. The tomographic apparatus according to claim 1, wherein both the filter length calculating device and the correction function calculating unit use a measured attenuation physical quantity for one transmission length of measured attenuation physical quantities for at least two transmission lengths measured by the attenuation physical quantity measuring device.

* * * * *